US007341844B2

(12) United States Patent
Fatemi

(10) Patent No.: US 7,341,844 B2
(45) Date of Patent: Mar. 11, 2008

(54) METHODS FOR DIAGNOSING AUTISM

(75) Inventor: S. Hossein Fatemi, Woodbury, MN (US)

(73) Assignee: Regents of the University of Minnesota, Saint Paul, MN (US)

(*) Notice: Subject to any disclaimer, the term of this patent is extended or adjusted under 35 U.S.C. 154(b) by 642 days.

(21) Appl. No.: 10/346,910

(22) Filed: Jan. 16, 2003

(65) Prior Publication Data

US 2003/0211556 A1    Nov. 13, 2003

Related U.S. Application Data

(60) Provisional application No. 60/349,846, filed on Jan. 16, 2002.

(51) Int. Cl.
*G01N 33/53*    (2006.01)
*G01N 33/537*    (2006.01)
*G01N 33/543*    (2006.01)
*G01N 33/542*    (2006.01)
*G01N 33/566*    (2006.01)
*G01N 33/567*    (2006.01)

(52) U.S. Cl. .................. 435/7.92; 435/7.1; 435/7.5; 435/7.7; 435/7.9; 438/501; 438/503

(58) Field of Classification Search ................ None
See application file for complete search history.

(56) References Cited

U.S. PATENT DOCUMENTS

| | | | |
|---|---|---|---|
| 3,817,827 A | 6/1974 | Benz | |
| 3,850,752 A | 11/1974 | Schuurs et al. | |
| 3,901,654 A | 8/1975 | Gross | |
| 4,098,876 A | 7/1978 | Piasio et al. | |

OTHER PUBLICATIONS

Tabor et al., 2001, Am J. Human Genetics, 69, No. 4, pp. 576.*
DSM-IV, Fourth Edition, APSA, 1994, Washington DC, Table of contents, three pages.*
Ausubel et al. (eds.), "Chapter 11: Immunology," *Short Protocols in Molecular Biology*, Fourth Edition, 1999, John Wiley & Sons, Inc., New York, pp. 11-1-11-30.
Cole et al., "The EBV-Hybridoma Technique and Its Application to Human Lung Cancer," *Monoclonal Antibodies and Cancer Therapy*, Reisfeld and Sell (eds.), 1985, Alan R. Liss, Inc., New York, pp. 77-96.
Cote et al., "Generation of human monoclonal antibodies reactive with cellular antigens," *Proc. Natl. Acad. Sci.* USA, 1983, 80:2026-2030.
de Bergeyck et al., "A panel of monoclonal antibodies against reelin, the extracellular matrix protein defective in reeler mutant mice," *J. Neurosci. Meth.*, 1998, 82:17-24.
Fatemi et al., "Reduction in Reelin immunoreactivity in hippocampus of subjects with schizophrenia, bipolar disorder and major depression," *Molecular Psychiatry*, 2000, 5:654-663.
Fatemi, "Reelin mutations in mouse and man: from reeler mouse to schizophrenia, mood disorders, autism and lissencephaly," *Mol Psychiatry*, 2001, 6:129-133.
Fatemi et al., "Altered levels of Reelin and its isoforms in schizophrenia and mood disorders," *NeuroReport*, 2001, 12(15):3209-3215.
Guidotti et al., "Decrease in Reelin and Glutamic Acid Decarboxylase$_{67}$ (GAD$_{67}$) Expression in Schizophrenia and Bipolar Disorder," *Arch. Gen. Psychiatry*, 2000, 57:1061-1069.
Guidotti et al., "New Neurochemical Markers for Psychosis: A Working Hypothesis of Their Operation," *Neurochemical Res.*, 2000, 25(9/10):1207-1218.
Hong et al., "Autosomal recessive lissencephaly with cerebellar hypoplasia is associated with human RELN mutations," *Nature Genetics*, 2000, 26:93-96.
Huse et al., "Generation of a Large Combinatorial Library of the Immunoglobulin Repertoire in Phage Lambda," *Science*, 1989, 246:1275-1281.
Ikeda and Terashima, "Expression of *reelin*, the Gene Responsible for the Reeler Mutation, in Embryonic Development and Adulthood in the Mouse," *Developmental Dynamics*, 1997, 210 :157-172.
Impagnatiello et al., "A decrease of reelin expression as a putative vulnerability factor in schizophrenia," *Proc. Natl. Acad. Sci, USA*, 1998, 95:15718-15723.
Köhler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4(3):72-79.
Lacor et al., "Reelin secretion from glutamatergic neurons in culture is independent from neurotransmitter regulation," *Proc. Natl. Acad. Sci. USA*, 2000, 97(7):3556-3561.
Lord et al., "Autism Diagnostic Interview-Revised: A Revised Version of a Diagnostic Interview for Caregivers of Individuals with Possible Pervasive Developmental Disorders," *J. Autism Dev. Disorders*, 1994, 24(5):659-685.
Ogawa et al., "The *reeler* Gene-Associated Antigen on Cajal-Retzius Neurons Is a Crucial Molecule for Laminar Organization of Cortical Neurons," *Neuron*, 1995, 14:899-912.
Persico et al., "Reelin gene allcles and haplotypes as a factor predisposing to autistic disorder," *Mol. Psychiatry*, 2001, 6:150-159.
Smalheiser et al., "Expression of reelin in adult mammalian blood, liver, pituitary pars intermedia, and adrenal chromaffin cells," *Proc. Natl. Acad. Sci. USA*, 2000, 97(3):1281-1286.
Stokstad, "New Hints Into the Biological Basis of Autism," *Science*, 2001, 294:34-37.
Fatemi et al., "Reduced Blood Levels of Reelin as a Vulnerability Factor in Pathophysiology of Autistic Disorder", *Cellular and Molecular Neurobiology*, 2002, 22(2):139-152.
Fatemi et al., "Dysregulation of Reelin and Bcl-2 Proteins in Autistic Cerebellum", *Journal of Autism and Developmental Disorders*, 2001, 31(6):529-535.
Fatemi et al., "Defective corticogenesis and reduction in Reelin immunoreactivity in cortex and hippocampus of prenatally infected neonatal mice", *Molecular Psychiatry*, 1999, 4:145-154.
Fatemi, "The role of Reelin in pathology of autism", *Molecular Psychiatry*, 2002, 7:919-920.

\* cited by examiner

*Primary Examiner*—Olga N. Chernyshev
(74) *Attorney, Agent, or Firm*—Fish & Richardson P.C.

(57) ABSTRACT

The invention relates to the use of Reelin as a marker for diagnosing psychiatric conditions. The disclosed tools and techniques can facilitate the diagnosis of psychiatric disorders including major depression, bipolar disorder, schizophrenia and autism.

6 Claims, No Drawings ant molecular mass of about 180 kDa is decreased

METHODS FOR DIAGNOSING AUTISM

CROSS REFERENCE TO RELATED APPLICATIONS

This application claims priority under 35 U.S.C. §119(e) of U.S. Application No. 60/349,846, filed Jan. 16, 2002.

TECHNICAL FIELD

This invention relates to the use of polypeptide markers for diagnosing psychiatric conditions.

BACKGROUND

Reelin is a glycoprotein that seems to have a role in central nervous system development. Reelin was discovered via studies of "reeler" mice, autosomal recessive mutants that have an ataxic and reeling gait. Reeler mice have numerous central nervous system defects, including cerebellar hypoplasia, abnormal neuronal positioning, aberrant orientation of cell bodies and fibers, inverted cortical lamination, and neuronal ectopia in laminated brain structures (e.g., cerebral and cerebellar cortices and hippocampus).

Neuroanatomical defects such as those observed in reeler mice can adversely affect synaptic connectivity and can impair normal brain function. Reelin levels are reportedly altered in the brains of some humans afflicted with major depression, bipolar disorder and schizophrenia, suggesting that Reelin may be involved in cell signaling systems underlying brain cognitive functions. See, e.g., Impagnatiello et al., 1998, Proc. Natl. Acad. Sci. USA, 95:15718-15723; Fatemi et al., 2000, Mol. Psychiatry, 5:654-663; Guidotti et al., Arch. Gen. Psychiatry, 57:1061-9; and Fatemi et al., 2001 Neuro. Report, 12:3209-3215.

SUMMARY

The methods and materials of the present invention can be used to facilitate diagnosis of psychiatric conditions. The invention is based, at least in part, on the discovery that blood levels of Reelin moieties are altered in patients afflicted with major depression, bipolar disorder, schizophrenia and autism. These and other psychiatric conditions can decrease the life quality of affected persons and can present a risk of harm to those affected and to others. Complicating matters, psychiatric disorders having different causal elements and different treatment protocols can have confusingly similar clinical symptoms. The disclosed tools and techniques can facilitate the diagnosis of psychiatric conditions and thereby improve therapy decisions and patient outcomes.

In one aspect, the invention features methods for diagnosing a psychiatric condition in a patient. The methods involve: comparing the level of at least one Reelin moiety in a biological sample from a patient with the level of a corresponding Reelin moiety in one or more control subjects, and diagnosing the condition based on the comparison. In some embodiments, the methods involve comparing the levels of two or more Reelin moieties in a biological sample from a patient with the levels of corresponding Reelin moieties in control subjects, and diagnosing the condition based on the comparison.

The psychiatric condition can be, for example, major depression, schizophrenia, bipolar disorder and autism. Suitable biological samples can include blood (including whole blood, plasma and serum), urine, and cerebral spinal fluid.

The levels of Reelin moieties in biological samples can be determined using an immunoassay (e.g., ELISA) that employs monoclonal or polyclonal antibodies to capture Reelin moieties. Reelin moieties can include, for example, full-length Reelin, natural proteolytic cleavage products of Reelin and post-translationally modified Reelin polypeptides. Particularly suitable Reelin moieties have apparent molecular masses of about 410 kDa, about 330 kDa and about 180 kDa.

A diagnosis of major depression can be made if the level of a Reelin moiety having an apparent molecular mass of about 410 kDa is not different from, or is increased relative to, control subjects, and the level of a Reelin moiety having an apparent molecular mass of about 180 kDa is decreased relative to control subjects. In addition, a diagnosis of major depression can be made if the level of a Reelin moiety having an apparent molecular mass of about 330 kDa is not different from, or is increased relative to, control subjects.

A diagnosis of major depression can be made if the level of a Reelin moiety having an apparent molecular mass of about 330 kDa is not different from, or is increased relative to, control subjects, and the level of a Reelin moiety having an apparent molecular mass of about 180 kDa is decreased relative to control subjects. A diagnosis of major depression also can be made if the level of a Reelin moiety having an apparent molecular mass of about 410 kDa is not different from, or is increased relative to, control subjects.

A diagnosis of major depression can be made if the level of a Reelin moiety having an apparent molecular mass of about 410 kDa is not different from, or is increased relative to, control subjects, and the level of a Reelin moiety having an apparent molecular mass of about 330 kDa is not different from, or is increased relative to, control subjects. A diagnosis of major depression also can be made if the level of a Reelin moiety having an apparent molecular mass of about 180 kDa is decreased relative to control subjects.

A diagnosis of schizophrenia can be made if the level of a Reelin moiety having an apparent molecular mass of about 410 kDa is increased relative to control subjects, and the level of a Reelin moiety having an apparent molecular mass of about 180 kDa is not different from, or is decreased relative to, control subjects. A diagnosis of schizophrenia also can be made if the level of a Reelin moiety having an apparent molecular mass of about 330 kDa is increased relative to control subjects.

A diagnosis of schizophrenia can also be made if the level of a Reelin moiety having an apparent molecular mass of 330 kDa is increased relative to control subjects, and the level of a Reelin moiety having an apparent molecular mass of about 180 kDa is not different from, or is decreased relative to, control subjects. A diagnosis of schizophrenia also can be made if the level of a Reelin moiety having an apparent molecular mass of about 410 kDa is increased relative to control subjects.

A diagnosis of schizophrenia can also be made if the level of a Reelin moiety having an apparent molecular mass of about 410 kDa is increased relative to control subjects, and the level of a Reelin moiety having an apparent molecular mass of about 330 kDa is increased relative to control subjects. A diagnosis of schizophrenia also can be made if the level of a Reelin moiety having an apparent molecular mass of about 180 kDa is not different from, or is decreased relative to, control subjects.

A diagnosis of bipolar disorder can be made if the level of a Reelin moiety having an apparent molecular mass of about 410 kDa is not different from, or is decreased relative to, control subjects, and the level of a Reelin moiety having an apparent molecular mass of about 180 kDa is decreased relative to control subjects. A diagnosis of bipolar disorder also can be made if the level of a Reelin moiety having an apparent molecular mass of about 330 kDa is decreased relative to control subjects.

A diagnosis of bipolar disorder can be made if the level of a Reelin moiety having an apparent molecular mass of about 330 kDa is decreased relative to control subjects, and the level of a Reelin moiety having an apparent molecular mass of about 180 kDa is decreased relative to control subjects. A diagnosis of bipolar disorder also can be made if the level of a Reelin moiety having an apparent molecular mass of about 410 kDa is not different from, or is decreased relative to, control subjects.

A diagnosis of bipolar disorder can be made if the level of a Reelin moiety having an apparent molecular mass of about 410 kDa is not different from, or is decreased relative to, control subjects, and the level of a Reelin moiety having an apparent molecular mass of about 330 kDa is decreased relative to control subjects. A diagnosis of bipolar disorder also can be made if the level of a Reelin moiety having an apparent molecular mass of about 180 kDa is decreased relative to control subjects.

A diagnosis of autism can be made if the level of a Reelin moiety having an apparent molecular mass of about 410 kDa is decreased relative to control subjects, and the level of a Reelin moiety having an apparent molecular mass of about 180 kDa is not different from, or is increased relative to, control subjects. A diagnosis of autism also can be made if the level of a Reelin moiety having an apparent molecular mass of about 330 kDa is not different from, or is increased relative to, control subjects.

A diagnosis of autism can be made if the level of a Reelin moiety having an apparent molecular mass of about 330 kDa is not different from, or is increased relative to, control subjects, and the level of a Reelin moiety having an apparent molecular mass of about 180 kDa is not different from, or is increased relative to, control subjects. A diagnosis of autism also can be made if the level of a Reelin moiety having an apparent molecular mass of about 410 kDa is decreased relative to control subjects.

A diagnosis of autism can be made if the level of a Reelin moiety having an apparent molecular mass of about 410 kDa is decreased relative to control subjects, and the level of a Reelin moiety having an apparent molecular mass of about 330 kDa is not different from, or is increased relative to, control subjects. A diagnosis of autism also can be made if the level of a Reelin moiety having an apparent molecular mass of about 180 kDa is not different from, or is increased relative to, control subjects.

The invention additionally features methods of diagnosing autism in an unborn child. Such a method includes comparing the level of at least one Reelin moiety in a biological sample from a biological parent or biological sibling of the unborn child with the level of a corresponding Reelin moiety in one or more control subjects, and diagnosing autism based on the comparison. Representative biological samples include whole blood, plasma, and serum.

An unborn child can be diagnosed with autism if the level of a Reelin moiety having an apparent molecular mass of about 410 kDa is decreased in the father relative to the control subjects, if the level of a Reelin moiety having an apparent molecular mass of about 330 kDa is not different in the father, or is increased in the father relative to, the control subjects, and/or if the level of a Reelin moiety having an apparent molecular mass of about 180 kDa is decreased in the father relative to the control subjects.

An unborn child also can be diagnosed with autism if the level of a Reelin moiety having an apparent molecular mass of about 410 kDa is decreased in the mother relative to the control subjects, if the level of a Reelin moiety having an apparent molecular mass of about 330 kDa is not different in the mother, or is increased in the mother relative to, the control subjects, and/or if the level of a Reelin moiety having an apparent molecular mass of about 180 kDa is decreased in the mother relative to the control subjects.

An unborn child also can be diagnosed with autism if the level of a Reelin moiety having an apparent molecular mass of about 410 kDa is decreased in the sibling relative to the control subjects, if the level of a Reelin moiety having an apparent molecular mass of about 330 kDa is not different in the sibling, or is increased in the sibling relative to, the control subjects, and/or if the level of a Reelin moiety having an apparent molecular mass of about 180 kDa is not different in the sibling, or is increased in the sibling relative to, the control subjects.

The invention also features articles of manufacture for diagnosing a psychiatric condition in a patient or in an unborn child. The articles of manufacture can include one or more anti-Reelin antibodies and packaging material, wherein the anti-Reelin antibodies can be used for determining Reelin levels in a patient, and wherein the packaging material includes a label or package insert indicating that the anti-Reelin antibodies can be used for diagnosing the condition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

The invention provides methods and materials for using Reelin as a marker to facilitate the diagnosis of psychiatric conditions in a patient. Psychiatric conditions relate to mental and emotional disorders. Neurological conditions relate to disorders of the nervous system. Some psychiatric conditions, referred to as neuropsychiatric conditions, have both neurological and psychiatric features. The term "psychiatric conditions," as used herein, refers to psychiatric and neuropsychiatric conditions. Psychiatric conditions are identified and classified in *Diagnostic and Statistical Manual of Mental Disorders, Fourth Edition, Revised: DSM-IV-TR,* Washington, D.C.: American Psychiatric Association; 2000. Neurological conditions that lack psychiatric features, such as lissencephaly, fall outside the meaning of "psychiatric condition."

The invention is based, at least in part, on the discovery that blood levels of Reelin moieties are altered in patients afflicted with psychiatric conditions, including major depression, bipolar disorder, schizophrenia and autism. The invention is also based in part on the discovery that blood levels of Reelin moieties are altered in the biological parents and biological siblings in patients afflicted with autism.

Reelin cDNA has been cloned from mouse and human (see, for example, GenBank Accession Nos. U79716 and U24703). The predicted 3461 amino acid polypeptides from mouse and human are 94% identical, suggesting that the mouse and human Reelin polypeptides are structurally and functionally similar. At its N-terminus, Reelin has a cleavable signal peptide followed by a segment similar to F-spondin. Reelin also has eight internal repeats of 350-390 amino acids, each containing an epithelial growth factor-like motif flanked by two related segments. The series of internal repeats is preceded by a hinge domain, and is followed by a highly basic 33 amino acid C-terminal domain.

Antibodies specifically reactive to Reelin have been produced and used for Western blotting and for immunocytochemical studies of Reelin stricture and function. See, e.g., Ogawa et al., 1995, *Neuron,* 14:890-912; DeBergeyck et al., 1998, *J. Neurosci. Meth.,* 82:17-24. Western blots using such antibodies indicate that several specifically immunoreactive Reelin moieties are present in biological samples. These moieties appear to correspond to full-length Reelin, and naturally occurring proteolytic cleavage products of full-length Reelin. Reelin moieties can be described by their apparent molecular weight, which can vary under different experimental conditions. Under the conditions described herein (see Example 1), full length Reelin has an apparent molecular mass of 410 kDa, and two naturally occurring variants of Reelin have apparent molecular masses of 330 kDa and 180 kDa.

In general, methods of the invention include determining the level of a Reelin moiety in a biological sample from a patient and comparing the level to that of one or more control subjects. Methods of the invention further include determining the level of a Reelin moiety in a biological sample from a biological parent or biological sibling of an unborn child (i.e., an embryo or a fetus) and comparing the level to that of one or more control subjects. Suitable biological samples for determining Reelin levels include, for example, blood (including whole blood, plasma and serum), urine, and cerebral spinal fluid.

A psychiatric condition is diagnosed based on comparing the level of at least one Reelin moiety relative to the level of a corresponding moiety (i.e., a Reelin moiety of equivalent molecular mass) in control subjects. Thus, it is determined if the level of a Reelin moiety is increased, decreased, or is not different than the level of a corresponding Reelin moiety in control subjects. Diagnostic accuracy can be improved by determining the levels of multiple reeling moieties.

Control subjects are individuals that are not affected by a psychiatric condition to be diagnosed. Control subjects can have traits similar to those of a patient to be diagnosed. For example, control subjects can include individuals of an ethnicity similar or identical to that of a patient to be diagnosed. In some embodiments, control subjects can include individuals of the same gender of a patient to be diagnosed. Control subjects also can include individuals of an age similar to that of a patient to be diagnosed. Control subjects also can include individuals that have resided in or near the past or present residence of a patient to be diagnosed.

Alternatively, a control subject can be an asymptomatic future patient. In this case control samples are obtained from a person prior to the onset of a psychiatric condition, and are preserved for future analysis. Such samples can be obtained, for example, prior to the birth of the future patient and throughout the lifetime of the future patient prior to manifestation of psychiatric symptomology.

The level of a Reelin moiety can be determined qualitatively (e.g., by visual observation of a Western blot) and compared with the level of a corresponding Reeling moiety in control subjects. A gross change in the level of at least one Reelin moiety compared to the level observed in control subjects can be diagnostic of a particular psychiatric disorder.

The level of a Reelin moiety also can be determined quantitatively (i.e., by measuring a signal attributable to a Reelin moiety and assigning a numerical value to the measured signal). Increases or decreases (e.g., at $p<0.05$ statistical significance) in the measured level of at least one Reelin moiety relative to the level measured in control subjects can be diagnostic of a particular psychiatric disorder.

Steady state blood levels of Reelin can be determined, for example, by quantitative immunoassay.

In patients having major depression, the steady state blood level of the 410 kDa Reelin moiety can be unchanged or increased by, for example, 15-55% (e.g., 15-55%, 25-45%, 30-40%, and 31-37%), relative to control subjects. In patients having major depression, the steady state blood level of the 330 kDa Reelin moiety can be unchanged or increased by, for example, 10-50% (e.g., 10-50%, 20-40%, 25-35%, and 27-33%), relative to control subjects. In patients having major depression, the steady state blood level of the 180 kDa Reelin moiety can be decreased by, for example, 10-50% (e.g., 10-50%, 20-40%, 25-35%, and 26-32%), relative to control subjects.

In schizophrenic patients, the steady state blood level of the 410 kDa Reelin moiety can be increased by, for example, 30-70% (e.g., 30-70%, 40-60%, 45-55%, and 46-52%), relative to control subjects. In schizophrenic patients, the steady state blood level of the 330 kDa Reelin moiety can be increased by, for example, 5-35% (e.g., 5-35%, 15-25%, and 19-25%), relative to control subjects. In schizophrenic patients, the steady state blood level of the 180 kDa Reelin moiety can be unchanged or decreased by, for example, 3-45% (e.g., 3-45%, 10-40%, 15-35%, and 20-30%), relative to control subjects.

In patients having bipolar disorder, the steady state blood level of the 410 kDa Reelin moiety can be unchanged or decreased by, for example, 15-55% (e.g., 15-55%, 25-45%, 30-40%, and 30-36%), relative to control subjects. In patients having bipolar disorder, the steady state blood level of the 330 kDa Reelin moiety can be decreased by, for example, 10-50% (e.g., 10-50%, 20-40%, 25-35%, and 27-33%), relative to control subjects. In patients having bipolar disorder, the steady state blood level of the 180 kDa Reelin moiety can be decreased by, for example, 30-70% (e.g., 30-70%, 40-60%, 45-55%, and 46-52%), relative to control subjects.

In autistic patients, the steady state blood level of the 410 kDa Reelin moiety can be decreased by, for example, 50-90% (e.g., 50-90%, 60-80%, 65-75%, and 67-73%), relative to control subjects. In autistic patients, the steady state blood level of the 330 kDa Reelin moiety can be unchanged or increased by, for example, 5-45% (e.g., 5-45%, 15-35%, 20-30%, and 24-30%), relative to control subjects. In autistic patients, the steady state blood level of the 180 kDa Reelin moiety can be unchanged or increased by, for example, 5-40% (e.g., 5-40%, 10-35%, 12-30%, 15-25%, and 17-22%), relative to control subjects.

Detecting Reelin Moieties

Reelin moieties can be detected by any protein detection technique. For example, Reelin moieties can be detected by a variety of routine immunological techniques. See, e.g., U.S. Pat. Nos. 3,817,827; 3,850,752; 3,901,654 and 4,098,876.

Antibodies useful for immunological detection can be polyclonal or monoclonal, and can be detectably labeled or unlabeled. Antibodies can be detectably labeled with radioactive molecules, fluorescent molecules, enzymes, enzyme substrates, enzyme cofactors, enzyme inhibitors and ligands (e.g., biotin and haptens). Unlabeled antibodies can be detected by, for example, agglutination assays. Unlabeled antibodies can also be used in combination with another reagent that can be used to detect the antibody, such as a detectably labeled antibody specifically reactive with the unlabeled antibody (e.g., anti-idiotype antibodies or other antibodies specific for an unlabeled immunoglobulin) or other reagent (e.g., detectably labeled protein A).

Antibodies having affinity for Reelin are available. See, e.g., Ogawa et al., 1995, *Neuron*, 14:890-912; and DeBergeyck et al., 1998, *J. Neurosci. Meth.*, 82:17-24. Additional Reelin-specific antibodies can be made as a matter of routine by one ordinarily skilled in the art.

Polyclonal antibodies can be obtained from the sera of immunized animals. Various host animals (e.g., rabbits, chickens, mice, guinea pigs and rats) can be immunized by injection of a Reelin moiety. Various adjuvants can be used to increase the immunological response of a host animal, including Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol.

Monoclonal antibodies can be obtained using a Reelin moiety and standard hybridoma techniques. In particular, monoclonal antibodies can be obtained by any technique that provides for the production of antibody molecules by cultured cell lines. See, e.g., Kohler et al., 1975, *Nature*, 256:495; Kosbor et al., 1983, *Immunology Today*, 4:72; Cole et al., 1983, *Proc. Natl. Acad. Sci. USA*, 80:2026; and Cole et al., 1983, *Monoclonal Antibodies and Cancer Therapy*, Alan R. Liss, Inc., pp. 77-96. Such antibodies can be of any immunoglobulin class including IgG, IgM, IgE, IgA, IgD, and any subclass thereof. Hybridomas can be cultivated in vitro and in vivo.

Antibody fragments having specific binding affinity for a Reelin moiety can be obtained as a matter of routine by one of ordinary skill in the art. Such fragments include, for example, F(ab')2 fragments that can be produced by pepsin digestion of the antibody molecule, and Fab fragments that can be generated by reducing the disulfide bridges of F(ab')2 fragments. Fab expression libraries can also be constructed. See, e.g., Huse et al., 1989, *Science*, 246:1275.

Antibodies and antibody fragments can be tested for specific binding to a Reelin moiety by standard immunoassay methods including ELISA, Radioimmunoassay and Western blotting. See, e.g., *Short Protocols in Molecular Biology*, Chapter 11, Green Publishing Associates and John Wiley & Sons, Ausubel et al., eds., 1992. Antibodies having specific binding affinity for a Reelin moiety are identified in a positive selection. Antibodies identified in such a selection can be negatively selected against another Reelin moiety, to identify antibodies having specific binding affinity for one Reelin moiety but not another Reelin moiety.

Reelin can be obtained in various ways for introduction into host animals for antibody production. For example, Reelin can be prepared from recombinant host cells. Typically, a nucleic acid molecule encoding Reelin is operably linked to transcriptional regulatory sequences in an expression vector and is then introduced into a host cell. Host cells can be prokaryotic or eukaryotic. Various host-vector systems suitable for the expression of proteins are known. See, e.g., Sambrook et al., 1989, *Molecular Cloning: A Laboratory Manual*, 2nd ed., Cold Spring Harbor Press, N.Y.; and *Current Protocols in Molecular Biology*, Ausubel et al., eds., Wiley and Sons, 1995. In addition to transcriptional regulatory sequences (e.g., promoters, enhancers, and terminators), expression vectors can include translational regulatory sequences, and a marker gene (e.g., conferring antibiotic resistance) suitable for selecting cells that contain the expression vector. Expression vectors can also include nucleotide sequences that encode a secretory sequence that directs the recombinant polypeptide to the secretory pathway of a host cell. Expression vectors can also include a nucleotide sequence encoding a purification molecule (e.g., GST, $HIS_6$ and FLAG) operably linked with the nucleic acid molecule encoding Reelin. Such vectors encode fusion polypeptides in which Reelin is covalently attached to a purification moiety that facilitates isolation from the recombinant host. Reelin can be purified using standard protein purification techniques.

Article of Manufacture For Diagnosing Psychiatric Conditions

Antibodies having specific binding affinity for a Reelin moiety can be combined with packaging material and sold as a kit for diagnosing psychiatric conditions in a patient or prenatally in an unborn child. An anti-Reelin antibody can be in a container (e.g., a capped tube or bottle made of plastic, polyethylene, polypropylene, ethylene, or propylene) or on a solid support (e.g., a microtiter plate). Kits can include two or more different anti-Reelin antibodies or fragments thereof. Kits typically contain instructions describing how the various reagents are effective for diagnosing psychiatric conditions. Components and methods for producing such kits are well known.

Kits can also include reagents for determining polypeptide levels in a biological sample, including, for example, antibodies having specific binding affinity to the particular polypeptide, secondary antibodies, and other useful agents for diagnosing psychiatric conditions. Other reagents that can be included in a kit include, for example, labeled, secondary antibodies that bind to an anti-Reelin antibody, indicator molecules, solid phases (e.g., beads), and buffers for washing or detecting Reelin.

The invention will be further described in the following examples, which do not limit the scope of the invention described in the claims.

EXAMPLES

Example 1

Reelin as a Diagnostic Marker for Major Depression, Schizophrenia and Bipolar Disorder This example demonstrates that blood Reelin levels can be used to facilitate the diagnosis of major depression, schizophrenia, and bipolar disorder.

Patients and Controls. Schizophrenic, bipolar and depressed patients were recruited from Fairview University Medical Center (FUMC), its affiliated clinics, and Community University Health Care Center. All patients were formally diagnosed according to the Diagnostic and Statistical Manual of Mental Disorders, Fourth Edition (DSM-IV) and were evaluated by using standard rating scales by board certified psychiatrists. Table 1 shows the demographic details of psychiatric patients and normal controls. Healthy age-matched control individuals were recruited from FUMC staff or from the surrounding community. The mean age of the control group was 37±16.4; the mean age of the schizophrenic patients was 40±10.9; the mean age of the bipolar patients was 40.6±7.0; and the mean age of the depressed patients was 40.5±14.7.

Blood (10-20 ml) was drawn from the antecubital vein into EDTA containing tubes (Allegiance), mixed well, and centrifuged at 3000 rpm for 15 min at 4° C. Plasma was collected, aliquoted, and frozen at −86° C. until assayed.

TABLE 1

Demographic data for psychiatric and control subjects

| Subject | Sex | Age | Ethnic Group[a] | Diagnosis | Medications[b] |
|---|---|---|---|---|---|
| C1 | M | 25 | C | — | — |
| C2 | F | 24 | C | — | — |
| C2 | F | 25 | C | — | — |
| C4 | M | 53 | C | — | — |
| C5 | M | 51 | C | — | — |
| C6 | F | 22 | C | — | — |
| C7 | F | 59 | C | — | — |
| S1 | M | 47 | C | Schizophrenia, Paranoid | Zol, Zypr, Seroq, Asm |
| S2 | M | 61 | C | Schizophrenia, Paranoid | Risp, Thoraz, Cog |
| S3 | M | 55 | C | Schizophrenia, Paranoid | Hald, Zypr |
| S4 | M | 55 | C | Schizophrenia, Paranoid | Stel, Traz, Cog |
| S5 | M | 32 | V | Schizophrenia, Paranoid | Prol IM, Olan, Klon |
| S6 | M | 29 | V | Schizophrenia, Paranoid | Hald IM, Olan, Clom |
| S7 | M | 32 | V | Schizophrenia, Paranoid | Hald IM, Olan |
| S8 | M | 37 | V | Schizophrenia, Paranoid | Cloz, Lith |
| S9 | M | 31 | V | Schizophrenia, Paranoid | Risp, Cog |
| S10 | F | 30 | H | Schizophrenia, Paranoid | Olan, Depak, Seroq |
| S11 | M | 25 | V | Schizophrenia, Paranoid | Olan, Pax, Akinet |
| S12 | M | 41 | V | Schizophrenia, Paranoid | Olan, Seroq |
| S13 | F | 32 | V | Schizophrenia, Paranoid | Olan, Pax, Traz |
| S14 | F | 52 | V | Schizophrenia, Paranoid | Olan, Cel |
| S15 | M | 41 | L | Schizophrenia, Residual | Hald IM, Olan |
| S16 | M | 39 | V | Schizophrenia, Residual | Cloz |
| B1 | F | 41 | C | Bipolar, Type I | Depak, Eff, Lam |
| B2 | M | 48 | C | Bipolar, Type I | Depak, Lit, Pax |
| B3 | M | 44 | C | Bipolar, Type II, rapid cycling | Depak, Eff |
| B4 | M | 41 | C | Bipolar, Type I | — |
| B5 | M | 29 | C | Bipolar, Type I | Lit |
| D1 | F | 26 | C | Major Depression, recurrent, treatment resistant | Bup, Eff |
| D2 | F | 58 | C | Major Depression, recurrent | Fluox |
| D3 | M | 47 | C | Major Depression, recurrent, treatment resistant | Depak, Nef, Eff |
| D4 | F | 31 | C | Major Depression, recurrent | Sert |

[a]C = Caucasian; V = Vietnamese; H = Hmong; L = Laotian
[b]Zol = Zolpidem; Zypr = Zyprexa; Seroq = Seroquel; Asm = Asmacort; Risp = Risperdal; Thoraz = Thorazine; Cog = Cogentin; Hald = Haloperidol; Stel = Stelazine; Traz = Trazodone; Cel = Celexa; Prol = Prolixin decanoate; IM = Intramuscular; Olan = Olanzapine; Klon = Klonopin; Clom = Clomipramine; Cloz = Clozapine; Lit = Lithium; Depak = Depakote; Pax = Paxil; Akinet = Akineton; Eff = Effexor; Lam = Lamictal; Bup = Bupropion; Fluox = Fluoxetine; Nef = Nefazodone; Sert = Sertraline Quantitative Western Blotting. A 0.2 ml frozen aliquot of serum was thawed, diluted in a buffer (10 mM PBS, 0.01 M SDS, and 1 mM phenanthroline in ethanol), mixed, and centrifuged at 1000×g 4 times for 30 min at 4° C. in a centricon YM-100 (Fisher) tube. The centricon tube was reversed and centrifuged at 1000×g for 2 min at 4° C. to remove the retentate. Protein concentrations were determined by the Bio-Rad Bradford assay using bovine serum albumin as a standard.

Different concentrations of retentate protein were dissolved in SDS-PAGE sample buffer under reducing conditions and heated at 97° C. for 10 min. Patient samples (30 μg protein) were loaded onto each lane of a 6% (29T/1C) resolving gel with a 3% (29T/1C) stacking gel. These samples were run in parallel with 15, 30, and 60 μg control plasma dilutions and Bio-Rad high molecular weight pre-stained standards at 75 V for 15 min, then 150 V for 75 min at room temperature. Protein was electroblotted onto nitrocellulose membranes (Hybond ECL, Amersham Pharmacia) at 150 mA for 15 hours at 4° C. Complete transfer was ascertained by staining duplicate gels with Coomassie Blue. Samples containing albumin and ceruloplasmin (30 μg protein) were loaded onto each lane of a 6% (29T/1C) resolving gel at 75 V for 15 min, then 150 V for 60 min and then blotted onto nitrocellulose membranes at 30 V for 120 min at room temperature.

Blots were blocked with 0.2% I-block (Tropix) in 0.3% Tween-20 PBS for 6 hours at room temperature (patient samples), or overnight at 4° C. (albumin and ceruloplasmin). Blots were incubated either with anti-Reelin antibody 142 (gift of Dr. Goffinet) at 1:200 dilution for 22 hours at 4° C., or with mouse anti human albumin/ceruloplasmin antibodies (Dako) at 1:20000 and 1:5000 dilutions for 1 hour at room temperature. Blots were then exposed to secondary antibody (sheep anti-mouse IgG coupled to horseradish peroxidase, 1:1000 dilution (Sigma) for Reelin, or goat anti-rabbit IgG coupled to horseradish peroxidase, 1:20000 dilution (Sigma) for albumin and ceruloplasmin) for 1 hour at room temperature. Between steps, immunoblots were washed for 30 min with a 0.5% Tween PBS solution.

Immune complexes were visualized using the ECL plus detection system (Amersham Pharmacia) and exposed to Hyperfilm ECL (Amersham Pharmacia). Sample densities were analyzed using a Bio-Rad densitometer and Bio-Rad Multi-Analyst software. Three Reelin immunoreactive bands having apparent molecular masses of 410 kDa (Reelin 410), 330 kDa (Reelin 330), and 180 kDa (Reelin 180) were observed for all control and psychiatric samples.

The densities of immunoreactive protein bands corresponding to albumin, ceruloplasmin, and Reelin 410, Reelin 330, and Reelin 180 were quantified with background subtraction. Quantification was performed blind to the nature of the samples. Control plasma samples (15-60 µg protein) were immunoblotted and quantified to verify that patient and control sample measurements were within the linear range of the assay. In general, the 180 kDa moiety was the most prevalent form, followed by 330 kDa and 410 kDa species in all samples examined.

Data were analyzed using InStatGraph Pad software (1993 version). Mann-Whitney and Student t-tests were used and a two-tailed p value was established to test for significance.

Results. Blood levels of Reelin moieties were altered in patients suffering from major depression, schizophrenia, and bipolar disorder. See Table 2.

the measured amount of Reelin 410 was observed in bipolar patients.

The observed alterations in blood Reelin levels do not appear to be artifactual because the measured amounts of the blood proteins ceruloplasmin and albumin did not differ significantly between psychiatric patients and control subjects.

These observations indicate that Reelin can be used as a blood marker for schizophrenia, major depression, and bipolar disorder.

Example 2

Reelin as a Diagnostic Marker for Autism

This example demonstrates that blood Reelin levels can be used to facilitate diagnosis of autism.

Patients and Controls. Frozen plasma or serum samples belonging to autistic twins, their siblings and parents previously drawn, either in EDTA containing tubes or clot-activated SST gel tubes (Fisher) following acquisition of parental consent from the Autism Genetic Resource Exchange (AGRE, Philadelphia, Pa.) program were obtained from 13 simplex families in which neither parent was affected with autism. Affected individuals included 12 pairs of identical twins and one set of quadruplets. Affected individuals were identified by AGRE examiners using DSM-IV and autism diagnostic interview (ADI) criteria (see, American Psychiatric Association, 1994, *Diagnostic and Statistical Manual of Mental Disorders,* Fourth Ed., American Psychiatric Press; and Lord et al., 1994, *J. Autisn. Dev. Disord.,* 24:659-685). Affected individuals were scored for behavioral pattern in three main areas: qualities of reciprocal social interaction; communication and language and restricted and repetitive, stereotyped interests and behaviors. Demographic data for all subjects and ADI subscores for autistic individuals are shown in Table 3.

TABLE 2

Steady state serum levels of Reelin moieties, Albumin and Ceruloplasmin

| Group | Reelin 410 | Reelin 330 | Reelin 180 | Ceruloplasmin | Albumin |
|---|---|---|---|---|---|
| Control | 2.22 ± 0.91 | 3.19 ± 1.06 | 7.46 ± 1.42 | 8.00 ± 2.43 | 86.64 ± 10.12 |
| Schizophrenia | | | | | |
| Vietnamese | 3.07 ± 1.02** | 2.87 ± 1.15 | 6.92 ± 1.45 | 9.98 ± 2.61 | 81.01 ± 10.73 |
| % Change | 37.98 | −9.94 | −7.28 | 24.78 | −6.50 |
| Caucasian | 3.64 ± 1.87 | 6.04 ± 0.76^ | 7.29 ± 1.81 | 9.72 ± 0.76 | 82.41 ± 4.06 |
| % Change | 63.58 | 89.67 | −2.27 | 21.56 | −4.88 |
| Hmong | 4.67 | 4.91 | 5.70 | 10.96 | 76.11 |
| % Change | 109.98 | 54.09 | −23.60 | 37.02 | −12.15 |
| Laotian | 3.16 | 4.28 | 8.24 | 13.84 | 85.89 |
| % Change | 41.92 | 34.28 | 10.45 | 73.11 | −0.87 |
| Combined | 3.32 ± 1.23* | 3.88 ± 1.71 | 7.02 ± 1.47 | 10.01 ± 2.36 | 81.4 ± 10.73 |
| % Change | 49.22 | 21.73 | −5.94 | 25.22 | −6.04 |
| Bipolar | 1.50 ± 0.88 | 2.21 ± 0.17^^ | 3.83 ± 2.67``  | 8.09 ± 1.35 | 79.01 ± 2.63 |
| % Change | −32.53 | −30.63 | −48.68 | 1.19 | −8.81 |
| Depression | 2.99 ± 0.61 | 4.14 ± 1.17 | 5.3 ± 1.15``` | 9.16 ± 1.07 | 81.37 ± 5.39 |
| % Change | 34.29 | 29.94 | −28.99 | 14.51 | −6.08 |

*vs. control: Mann-Whitney, p = 0.0225
**vs. control: Mann-Whitney, p = 0.0431
^vs. control: Mann-Whitney, p = 0.0061
^^vs. control: Mann-Whitney, p = 0.0480
``vs. control: Student's t-test, p = 0.0117
```vs. control: Mann-Whitney, p = 0.0424

The measured amount of Reelin 410 in schizophrenic patients (Caucasian, Vietnamese, Hmong and Laotian) was 49% greater (p<0.02) than in control subjects. An upward trend in the measured amount of Reelin 330 was also observed in the combined schizophrenic group (the exception being a small decrease in the Vietnamese patient). A downward trend in the measured amount of Reelin 180 was observed in the combined schizophrenic group, except for a small increase in the Laotian patient.

The measured amount of Reelin 180 in depressed patients was 29% lower (p<0.04) than in control subjects. A downward trend in the measured amount of Reelin 410 and Reelin 330 was observed in depressed patients.

The measured amount of Reelin 330 in bipolar patients was 31% lower (p<0.048) than in control subjects. The measured amount of Reelin 180 in bipolar patients was 49% lower (p<0.011) than in control subjects. An upward trend in

TABLE 3

Demographic data for all subjects and ADI subscores for autistic individuals

| Group | Age | Sex | Social | Comm. V | Comm. NV | Behavior | Onset | Seizure |
|---|---|---|---|---|---|---|---|---|
| Control, N = 8 | 38.3 ± 15.6 | 4M/4F | | | | | | |
| Fathers, N = 13 | 38.7 ± 7.5 | 13M | | | | | | |
| Mothers, N = 13 | 36.6 ± 6.1 | 13F | | | | | | |
| Autistic, N = 28 | 11.4 ± 2.1 | 22M/6F | 22.3 ± 4.2 | 18 ± 2.7 | 12.7 ± 2.1 | 6.0 ± 2.6 | 3.6 ± 1.6 | N = 6 |
| Siblings, N = 6 | 7.3 ± 3.3 | 3M/3F | | | | | | |

The mean age of twins was 7.42±2.1 (M±SD years) at blood draw, 6 were females, 24 males, all were identical twins; 6 had comorbid seizures (two had fever-associated seizures). The mean ages of family members at the time of blood draw were: fathers (38.7±7.5 years), mothers (36.6±6.1 years) and siblings (7.3±3.3 years).

Control blood samples were drawn from staff and employees of the University of Minnesota Medical School following approval of protocol by the Institutional Review Board of the University of Minnesota and obtaining of consent and review of their medical histories. Control blood (10-20 ml) was drawn from the antecubital veins into EDTA-containing tubes (Allegiance), mixed well, and centrifuged at 3000 rpm for 15 min at 4° C. Plasma was collected, aliquoted, and frozen at −86° C. until assayed. The mean age of control individuals was 38.3±15.6 years. None of the control individuals had any first-degree relatives with autism, and none of the control subjects was taking psychotropic medication except for one who was receiving low dose nortriptyline for treatment of migraine.

Quantitative Western Blotting. One microliter of each serum sample was thawed, adjusted for protein content following Bradford assay (bovine serum albumin standard), diluted in SDS-PAGE sample buffer under reducing conditions, and heated at 97° C. for 10 min. Protein samples (30 μg/lane) were loaded onto each lane of a 6% (25T/1C) resolving gel with a 3% stacking gel (29T/1C) and run in parallel with 15, 30, and 60 μg of control plasma dilutions and with Amersham high molecular weight pre-stained standards at 75 volts for 15 min and later 150 volts for 75 min at room temperature (RT). Protein was electroblotted onto nitro-cellulose membranes (Hybond ECL, Amersham Pharmacia) at 150 mA for 15 hours at 4° C. and complete transfer was verified by staining duplicate gels with Coomassie Blue. In addition, protein samples containing albumin and ceruloplasmin (30 μg/lane) were loaded onto each lane of a 6% resolving gel (29T/1C) with a 3% stacking gel at 75 V for 15 min, then 150 V for 60 min at room temperature and later blotted onto nitro-cellulose membranes at 30 V for 120 min at room temperature. Blots were blocked for 6 hours at room temperature with 0.2% I-block (Tropix) in 0.3% Tween-20 PBS (Reelin) or overnight at 4° C. (albumin and ceruloplasmin). Blots were incubated with anti-Reelin antibody #142 (gift of Dr. Goffinet) at 1:200 dilution for 22 hr at 4° C., or with mouse anti-human albumin/ceruloplasmin antibodies (Dako) at 1:20000 and 1:5000 dilutions for 1 hr at room temperature. Secondary antibody (sheep anti-mouse IgG coupled to horseradish peroxidase, 1:1000 (Sigma) for Reelin, or goat anti-rabbit IgG coupled to horseradish peroxidase, 1:20000 (Sigma) for albumin and ceruloplasmin) was added for 1 hr at room temperature. Between steps the blots were washed for 30 min with a 0.5% Tween PBS. Immune complexes were visualized using ECL plus (Amersham Pharmacia) and exposed to Hyperfilm ECL (Amersham Pharmacia).

Sample densities were analyzed using a Bio-Rad densitometer and the Bio-Rad Multi-Analyst software. Analysis of 15 μg-60 μg control samples confirmed that all samples fell within the linear range of the densitometric curve for Reelin. Three Reelin immunoreactive bands having apparent molecular masses of approximately 410 kDa (Reelin 410), 330 kDa (Reelin 330) and 180 kDa (Reelin 180) were observed for all control and test samples. Densitometry and background subtraction performed blind to the identity of the samples.

Statistical Analysis. Data were analyzed using the SPSS 10.1 program for Windows. An alpha level of 0.05 was used for all statistical tests.

Reelin moiety determinations did not significantly differ between twins (paired samples t-tests), and aggregated mean values for each pair of twins were used in statistical analyses. The distribution of the samples (controls, aggregated twins, mothers, fathers, and non-autistic siblings) and the homogeneity of their variances were examined to determine the appropriateness of parametric tests. With regard to sample distributions, significant skewness and kurtosis were observed only for Reelin 410 determinations for twins, fathers, and mothers. Variances significantly differed between groups for Reelin 180 determinations (Levene Statistic (4, 48)=4.99, p=0.002), and Reelin 330 determinations (Levene Statistic (4, 48)=3.56, p=0.013). Therefore, more conservative non-parametric tests and correlations were used to analyze Reelin 410, Reelin 330, and Reelin 180 levels, and parametric tests were used for albumin and ceruloplasmin.

To evaluate overall differences between controls and family members, Kruskal-Wallis one-way analyses of variance were used to analyze Reelin 410, Reelin 330, and Reelin 180 determinations, and analyses of variance were used to analyze albumin and ceruloplasmin determinations. Evaluations of overall differences in protein levels between groups were followed up by Mann-Whitney tests to identify significant differences.

To evaluate overall differences among family members, Friedman tests were used to analyze Reelin 410, Reelin 330, and Reelin 180 determinations, and repeated measures analyses of variance were used to analyze albumin and ceruloplasmin determinations. Non-autistic siblings were excluded from Friedman tests and repeated measures analyses because the size of this group was limited (N=6). Twins and non-autistic siblings were analyzed separately. Evaluations of overall differences in protein levels among family members were followed up by Wilcoxon tests to identify significant differences.

Results. Blood levels of Reelin moieties were altered in patients suffering from autism, and in family relatives. See Table 4.

TABLE 4

Steady state levels of Reelin moieties, albumin and ceruloplasmin in serum

| Group | Reelin 410 % Change | Reelin 330 % Change | Reelin 180 % Change | Ceruloplasmin % Change | Albumin % Change |
|---|---|---|---|---|---|
| Control | 1.59 ± 0.68 | 2.85 ± 0.68 | 2.35 ± 0.48 | 8.00 ± 2.43 | 86.64 ± 10.12 |
| Father | 0.61 ± 0.46 −62$^a$ | 3.18 ± 2.03 12 | 1.60 ± 0.72 −32$^{b,c}$ | 9.36 ± 3.07 17.04$^d$ | 87.72 ± 17.29 1.25 |
| Mother | 0.45 ± 0.29 −72$^a$ | 3.29 ± 2.33 15 | 1.54 ± 0.61 −34$^{b,c}$ | 9.92 ± 3.29 24.06 | 86.41 ± 20.73 −0.27 |
| Twin A | 0.44 ± 0.21 −72 | 3.21 ± 2.08 13 | 2.64 ± 1.43 12 | 10.65 ± 3.46 33 | 88.62 ± 19.63 2.29 |
| Twin B | 0.52 ± 0.24 −67 | 3.77 ± 2.24 32 | 2.70 ± 1.13 15 | 10.71 ± 3.18 33 | 89.52 ± 14.07 3.33 |
| Twins A & B | 0.48 ± 0.23 −70$^a$ | 3.64 ± 2.06 27 | 2.71 ± 1.27 15 | 10.86 ± 3.32 35.75 | 88.86 ± 17.21 2.56 |
| Siblings | 0.47 ± 0.43 −70$^a$ | 3.58 ± 2.72 25 | 2.75 ± 1.66 17 | 10.31 ± 2.09 28.97 | 92.04 ± 14.52 6.24 |

$^a$p < 0.01 vs. controls, Mann-Whitney test, two-tailed;
$^b$p < 0.05 vs. controls, Mann-Whitney test, two-tailed;
$^c$p < 0.01 vs. twins, Wilcoxon signed ranks test, two-tailed;
$^d$p < 0.05 vs. twins, paired t-test, two-tailed.

The measured amount of Reelin 410 was lower in autistic twins (−70%, p<0.01), their fathers (−62%, p<0.01), their mothers (−72%, p<0.01) and their phenotypically normal siblings (−70%, p<0.01) relative to control subjects. Kruskal-Wallis one-way analyses of variance between controls, twins, fathers, mothers, and siblings revealed an overall significant difference between groups for determinations of Reelin 410 ($\chi^2$ (4, N=53)=18.55, p=0.001). Follow-up Mann-Whitney tests revealed significant differences between twins and control subjects (U=2.0, N=21, p<0.001), fathers and control subjects (U=7.0, N=21, p=0.001), mothers and control subjects (U=3.0, N=21, p<0.001), and non-autistic siblings and control subjects (U=3.0, N=14, p=0.007).

An upward trend in the measured amount of Reelin 330 was observed in all family members relative to control subjects.

A slight upward trend in the measured amount of Reelin 180 was observed in autistic individuals relative to control subjects. The measured amount of Reelin 180 was also greater in family members relative to control subjects, except for parents, whose values were moderately lower. Kruskal-Wallis one-way analyses of variance between controls, twins, fathers, mothers, and siblings revealed an overall significant difference between groups for determinations of Reelin 180 ($\chi$2 (4, N=53)=13.01, p=0.011). Follow-up Mann-Whitney tests revealed significant differences between fathers and control subjects (U=21.0, N=21, p=0.025), and mothers and controls (U=19.0, N=21, p=0.016).

These observations indicate that Reelin can be used as a blood marker for autism.

Example 3

Genotyping RELN Gene Exon 6 Alleles in Autistic Families and Controls

This Example demonstrates that the polymorphisms within the nucleic acid sequences encoding Reelin can be used to facilitate the diagnosis of autism.

Patients and Controls. An A/G transversion polymorphism was previously described (Persico et al., 2001, Mol. Psych., 6:150-9) in the 6$^{th}$ exon of the human RELN gene that generates a restriction site for PvuII. This polymorphism was examined using genomic DNA from 9 subjects with autism, 13 first degree relatives (AGRE consortium) and 5 controls and PCR to amplify a 202 bp fragment containing the polymorphic site.

Analysis of Polymorphisms Using PCR. The following oligonucleotide primers were used for the PCR amplification: (sense) 5'-ACA GCA TGT TGG CAC TTG TG-3' (SEQ ID NO:1); and (antisense) 5'-GTG AGG AAT GTT CCT GTA AC-3' (SEQ ID NO:2). The PCR reaction was modified from that described in Persico et al. and was performed using the following reagents: 400 mM dATP, dCTP and dTTP, 300 mM dGTP, 25 mM 7-deaza-dGTP, 50 pmoles of each primer, 300 ng of DNA and 5 U Taq DNA Polymerase (NEB) in a buffering solution of 10 mM KCl, 10 mM $(NH_4)_2SO_4$, 20 mM Tris-HCl, 2 mM $MgSO_4$, 0.1% Triton X-100 at a pH of 8.8 with 10% DMSO in a total reaction volume of 100 ml. The reaction conditions for PCR amplification consisted of 35 cycles of: 95° C. for 30 sec, 54° C. for 30 sec, 72° C. for 1 min, and 72° C. for 5 min. PCR products were then digested using 10 U of PvuII (NEB) in 40 μl of buffered solution (50 mM NaCl, 10 mM Tris-HCl, 10 mM $MgCl_2$, 1 mM dithiothreitol, pH 7.8) for 1.5 hrs at 37° C. Undigested and digested PCR products were electrophoresed on a 10% polyacrylamide gel using TBE buffer (89 mM Tris, 89 mM boric acid, 2 mM EDTA) for 2 hr at 80V. Gels were stained with ethidium bromide and visualized using a BioRad GelDoc system.

Results. From the 5 autistic families, 22% of autistic subjects (2/9) were homozygous for the A1 allele in RELN exon 6 (a 202 bp fragment after digestion), 44% (4/9) were homozygous for the A2 allele (125 bp and 77 bp fragments after digestion) and 33% (3/9) were heterozygous for the A1 and A2 alleles (202 bp, 125 bp, and 77 bp fragments after digestion). Persico et al. previously showed that approximately 50% of the autistic subjects they examined exhibited the A1 allele for exon 6 of the RELN gene. Interestingly, all first-degree relatives of the family with two autistic subjects carrying the A1 allele also exhibited the same allele. None of the 5 controls showed the A1 allele.

These observations indicate that genotyping of the RELN gene can be used diagnostically.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

```

What is claimed is:

1. A method for diagnosing autism in a patient, said method comprising:

determining the level of at least one Reelin moiety in a biological sample from said patient, wherein said at least one Reelin moiety is chosen from a first Reelin moiety having an apparent molecular weight of about 410 kDa, a second Reelin moiety having an apparent molecular weight of about 180 kDa, and/or a third Reelin moiety having an apparent molecular weight of about 330 kDa, wherein said biological sample is selected from the group consisting of whole blood, plasma, and serum;

comparing said at least one Reelin level in said patient with the level of a corresponding Reelin moiety in one or more control subjects; and diagnosing said autism in said patient if:

(a) when the levels of said first and said second Reelin moieties are determined, the level of said first Reelin moiety in said patient is decreased relative to control subjects and the level of said second Reelin moiety in said patient is not different from, or is increased relative to, said control subjects;

(b) when the levels of said third and said second Reelin moieties are determined, the level of said third Reelin moiety in said patient is not different from, or is increased relative to, control subjects and the level of said second Reelin moiety in said patient is not different from, or is increased relative to, said control subjects; and/or (c) when the levels of said first and said third Reelin moieties are determined, the level of said first Reelin moiety in said patient is decreased relative to control subjects and the level of said third Reelin moiety in said patient is not different from, or is increased relative to, said control subjects.

2. The method of claim 1, wherein the diagnosis of autism is confirmed if:

in step (a), when the level of said third Reelin moiety is further determined, the level of said third Reelin moiety in said patient is not different from, or is increased relative to, said control subjects;

in step (b), when the level of said first Reelin moiety is further determined, the level of said first Reelin moiety in said patient is decreased relative to said control subjects; and/or in step (c), when the level of said second Reelin moiety is further determined, the level of said second Reelin moiety in said patient is not different from, or is increased relative to, said control subjects.

3. The method of claim 1, wherein said level(s) is/are determined using an immunoassay.

4. The method of claim 3, wherein said immunoassay is an ELISA.

5. The method of claim 3, wherein said at least one Reelin moiety is captured with a polyclonal anti-Reelin antibody.

6. The method of claim 3, wherein said at least one Reelin moiety is captured with a monoclonal anti-Reelin antibody.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
acagcatgtt ggcacttgtg                                                      20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
gtgaggaatg ttcctgtaac                                                      20
```